United States Patent [19]

Zirngibl et al.

[11] 3,947,584

[45] Mar. 30, 1976

[54] NOVEL INDOLYL ALKYL AMINES, METHOD OF PRODUCING SAME, AND THEIR USE AS ANORECTIC AGENTS

[75] Inventors: Ludwig Zirngibl, Zofingen; Rudolf Adrian, Vordemwald; Ulrich Jahn, Zofingen, all of Switzerland

[73] Assignee: Siegfried Aktiengesellschaft, Zofingen, Switzerland

[22] Filed: Sept. 17, 1973

[21] Appl. No.: 397,779

[30] Foreign Application Priority Data
Sept. 15, 1972 Switzerland................ 13517/72

[52] U.S. Cl............................ 424/274; 260/326.15
[51] Int. Cl.[2]................................ A61K 31/40
[58] Field of Search................................ 424/274

[56] References Cited
FOREIGN PATENTS OR APPLICATIONS

| | | |
|---|---|---|
| 886,684 | 1/1962 | United Kingdom |
| 974,894 | 11/1964 | United Kingdom |
| 990,092 | 4/1965 | United Kingdom |

*Primary Examiner*—Norman A. Drezin
*Attorney, Agent, or Firm*—Milton Osheroff

[57] ABSTRACT

Indolyl alkyl amines of the following formula:

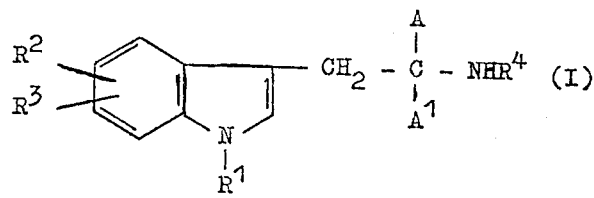

and their salts with organic or inorganic acids. In this formula I, A and $A^1$ denote identical or different alkyl radicals which both together have a total of 3–8 C-atoms. $R^1$ denotes hydrogen, a lower alkyl radical having up to 4 C-atoms or a possibly substituted benzyl or benzoyl radical. $R^2$ and $R^3$ may be the same or different and denote hydrogen, a halogen (more particularly chlorine, bromine or fluorine) or (possibly halogenated) lower alkyl radicals or (possibly etherified) hydroxy radicals. $R^4$ denotes hydrogen, a lower alkyl radical, an acyl group or a (possibly substituted) benzyl radical or the cyano-ethyl group. The compounds are useful as anoretics (appetite inhibitors) and can be made by various disclosed methods.

1 Claim, No Drawings

NOVEL INDOLYL ALKYL AMINES, METHOD OF PRODUCING SAME, AND THEIR USE AS ANORECTIC AGENTS

This invention relates to novel indolyl alkyl amines of the general formula

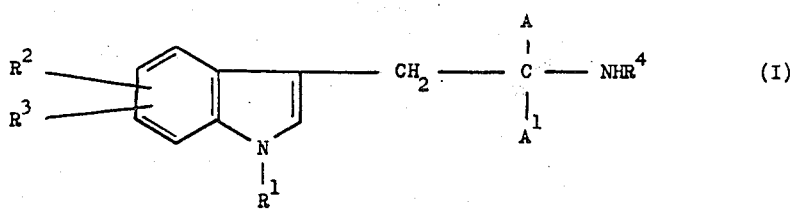

and their salts with organic or inorganic acids. In this formula I, A and $A^1$ denote identical or different alkyl radicals which both together have a total of 3–8 C-atoms. $R^1$ denotes hydrogen, a lower alkyl radical having up to 4 C-atoms or a possibly substituted benzyl or benzoyl radical. $R^2$ and $R^3$ may be the same or different and denote hydrogen, a halogen (more particularly chlorine, bromine or fluorine) or (possibly halogenated) lower alkyl radicals or (possibly etherified) hydroxy radicals. $R^4$ denotes hydrogen, a lower alkyl radical, an acyl group or a (possibly substituted) benzyl radical or the cyano-ethyl group. The compounds represented by Formula I and their salts (in particular the 3-(2'-amino-2'-methylbutyl)-indole and the salts of same such as the hydrochloride salt) are useful as anorectic agents for a method of inhibiting or reducing appetite in mammals and human beings.

The novel compounds of the invention are preferably prepared by reacting a gramine which is possibly substituted with $R^2$ and/or $R^3$ at the benzene ring, with a nitroparaffin, the nitro-group of which is fixed to a non-terminal C-atom, whereupon the 3-nitroalkyl indol which forms as intermediate is condensed with a compound of the formula $R^1$—X (where X denotes a radical liberated under condensation conditions, for example a halogen or an aryl-sulphonic acid radical), if desired, for the purposes of introducing a substituent $R^1$ other than H into the ring nitrogen, and then the nitro-group is reduced to the amino-group, whereupon if required a radical $R^4$ other than H is introduced into the amino-group. The resulting primary or secondary amines can then, if required, be converted to the corresponding salts by the action of organic or inorganic acid.

If it is desired to introduce a substituent $R^4$ other than hydrogen into the primary amino group formed during the reduction, the method to be applied naturally depends on the nature of the required substituent $R^4$. If, for example, $R^4$ is to be the cyano-ethyl group, the primary amine is reacted with acrylonitrile under conditions which favour an addition reaction. If the group $R^4$ is to be a hydrocarbon radical, the primary amine is most conveniently reacted with a reactive ester of a carboxylic acid whose acyl radical gives the required hydrocarbon radical by hydrogenation, whereupon the acyl amine forming as condensation product is hydrogenated. Reactive carboxylic acid esters useable for this purpose are, for example, phenyl formate or benzoyl chloride. Condensation of these with the primary amine, for example the 3-(2'-methyl-2'-aminobutyl)-indole formed by reduction of the nitro group, results in intermediates, whose amino-group is substituted with the formyl radical or the benzoyl radical respectively. Hydrogenation thereof, preferably with lithium aluminium hydride, gives the corresponding 3-(2'-methyl-2'-methylaminobutyl)- and 3-(2'1 methyl-2'-benzylaminobutyl)-indole.

Examples of indolyl alkyl amines obtained with the process according to the invention using 2-nitrobutane are: 3-(2'-methyl-2'-aminobutyl)-indole, which may also be termed α-methyl-α-ethyl tryptamine, and also 3-(2'-methyl-2'-methylaminobutyl)-indole, 3-(2'-methyl-2'-aminobutyl)-5-chloro-indole, 3-(2'-methyl-2'-aminobutyl)-5-methyl-6-chloro-indole, 3-(2'-methyl-2'-acetylaminobutyl)-5-trifluoro-indole, 3-(2'-methyl-2'-benzylaminobutyl-indole and 3-(2'-methyl-2'-methylbutyl)-5-ethoxy-indole. If gramine is reacted with 2-nitropentane, reduction of the primary 3-(2'-methyl-2'-nitropentyl)-indole leads to 3-(2'-methyl-2'-aminopentyl)-indole or α-methyl-α-propyl tryptamine, while the use of 3-nitropentane results in 3-(2'-ethyl-2'-aminobutyl)-indole or α,α-diethyltryptamine. Examples of products obtained using nitroparaffins of a higher number of carbon atoms are: 3-(2'-propyl-2'-aminopentyl)-indole, 3-2'-ethyl-2'-aminohexyl)-indole, 3-(2'-butyl-2'-aminohexyl)-indole, 3-(2'-methyl-2'-aminoheptyl)-indole, 3-(2'-ethyl-2'-aminooctyl)-indole and 3-(2'-methyl-2'-aminononyl)-indole.

Similar derivatives of tryptamine as obtained with the process according to the invention have already been described in considerable numbers and have been examined in respect of pharmacodynamic properties, of., particularly British patent specification nos. 974,894 and 990,092 and J. Chem. Soc. 1965, 7164 ff. and 7179 ff.; Br. J. Pharmac. Chemother. (1967) 29, 70 ff. The stimulant properties on the central nervous system as determined for a number of indolyl alkyl amines and functional derivatives thereof were the main focus of interest. α-Alkyl tryptamines have in fact already appeared on the market as stimulants and anti-depressants, but have had to be withdrawn, in some cases because of undesirable side-effects. The known indolyl alkyl amines and indolyl hydroxyl amines have also been found to have anorectic (appetite inhibiting) effects, which have been described but which are, without exception, so overshadowed by stimulant, sympathicomimetic, mono-aminoxidase-inhibiting, motility-increasing and in some cases even hallucinogenic effects that it was not possible to think of using these compounds as appetite-inhibiting drugs.

It has now surprisingly been found that a relatively narrow sub-group of the class of substituted tryptamine derivatives, namely the α,α-dialkyl tryptamines, has a pharmacodynamic behaviour which clearly differs qualitatively. Its most striking feature is that the anorectic effect predominates over a stimulating effect to an astonishing degree. This has obviously gone unrecognized because those representatives of the said sub-group which exhibit this feature to the optimum extent have not hitherto been prepared or described. These novel compounds correspond to the general formula I indicated hereinbefore.

In order to show how clearly $\alpha,\alpha$-dialkyl tryptamines obtainable according to the invention are superior to the most closely related known tryptamine derivative ($\alpha,\alpha$-dimethyl tryptamine) in respect of the gap between the anorectic and the toxic effects, the following Table 1 gives some results of animal experiments with a single application of the substances dissolved in equivalent quantities of HCl. The first column gives the respective two alkyl groups which are fixed in the $\alpha$-position to the otherwise unsubstituted tryptamines.

Table 1

| $\alpha$-Substituents | Toxicity LD 50 Mouse, oral mg/kg | Anorexia ED 50 Rat, oral mg/kg | Therapeutic Index (LD 50 ED 50) |
| --- | --- | --- | --- |
| Methyl, ethyl | 700 | 15 | 47 |
| Ethyl, ethyl | 620 | >50 | <12 |
| Methyl, propyl | 530 | approx. 50 | approx. 11 |
| Propyl, propyl | 900 | >>50 | <<18 |
| known comparison substance: | | | |
| Methyl, methyl | 320 | 36 | 9 |

The quantitatively comparative numerical values given in Table 1 illuminate only one partial aspect of the properties of compounds obtainable according to the invention. These properties also differ so clearly in many respects qualitatively both from the chemically related compounds and from the present-day conventional anorectics that they can be designated therapeutically applicable appetite-inhibitors of a new type. In particular, their pharmacological behaviour differs from that of the present-day anorectics of the phenyl ethyl amine or amphetamine group due to the absence of sympathicomimetic-cardiovascular and motor-stimulating effects. They attenuate the orientation motility and the fighting behaviour of mice, lower the blood pressure of cats and dogs, have a bradycardic effect, reduce the contraction amplitude of isolated guinea pig heart, and in the majority of the experiments lower the pressure in the right ventricle of the heart and in the pulmonary artery of narcotized cats and dogs, and thus their effect is the exact opposite of the amphetamine type of anorectics which have a predominantly sympathicomimetic action on the circulation. Since some representatives of this class of substance are today regarded as responsible for the occurrence of primarily pulmonary hypertonia in man, the different type of behaviour pharmacologically on the circulation as exhibited by the substances obtainable according to the invention could be very important.

EXAMPLE 1

A mixture of 34.8 g (200 mM) of gramine, 242.5 ml of 2-nitrobutane and 9 g of solid sodium hydroxide was heated to reflux temperature in a nitrogen atmosphere for 8 hours. The mixture was suction-filtered after cooling. The pH of the filtrate was adjusted to 4 with 10% acetic acid (80 ml) and the filtrate was washed with five times 180 ml of water. The organic phase was treated with activated charcoal and then dried with sodium sulphate. Evaporation yielded 43.4 g of residue having a melting point of 69°–73°C. This was chromatographed on 15 times the quantity of aluminium oxide activity III. Evaporation of the combined benzene eluates gave 36.6 g of product having a melting point of 76.5–78.5°C. (yield: 79% of the theoretical), from which 3-(2'-methyl-2'-nitrobutyl)-indole was obtained by recrystallising from benzine to a constant melting point of 79°–81°C.

Calculated for $C_{13}H_{16}N_2O_2$ (232.3): 13.77% O.
Found: $C_{12.8}H_{15.4}N_2$ 13.75% O.

Reduction: A mixture of 35.5 g (152.4 mM) of 3-(2'-methyl-2'-nitrobutyl)-indole and 3.55 g of platinum on activated charcoal (5%) and 400 ml of ethanol was hydrogenated initially at room temperature and 100 atmospheres $H_2$ initial pressure, whereupon heating was continued for 1 hour at 100°C. After filtration of the mixture, the filtrate was evaporated and yielded about 31 g of product having a melting point of 80°–84°C., which after being recrystallised twice from xylene yielded 18.45 g of 3-(2'-amino-2'-methylbutyl)-indole having a melting point of 111.5°–112.5°C. in the form of fine, flat, colourless needles. (Yield: 60% of the theoretical.)

Calculated for $C_{13}H_{18}N_2$ (202.3).
Found: $C_{12.95}H_{17.4}N_2$.

EXAMPLE 2

If the unsubstituted gramine is replaced by the corresponding quantity of 5-methoxygramine and if the procedure is otherwise identical to Example 1, the intermediate obtained is 3-(2'-methyl-2'-nitrobutyl)-5-methoxy-indole in the form of needles having a melting point of 125°C. (from cyclohexane).

Calculated for $C_{14}H_{18}N_2O_3$ (262.3): 64.12 C, 6.92 H, 10.67 N, 18.29 O.
Found: 64.41 C, 7.01 H, 10.71 N, 17.87 O.

The corresponding amine (melting point uncertain) was obtained therefrom by reduction. Melting point of the hydrochloride salt 222°–225°C. (from ethylacetate); melting point of succinate 157°C. (insoluble in ether).

EXAMPLE 3

2.5 g of sodium was dissolved in 200 ml of absolute ethanol in a 500 ml 3-neck flask provided with a dropping funnel with a drying tube, an internal thermometer and an agitator, and 11.3 g (110 mM) of 2-nitrobutane and 17.4 g (110 mM) of gramine were added. A solution of 19.2 ml (202 mM) of dimethyl sulphate in 50 ml of absolute ethanol was then added dropwise over a period of 40 minutes and at an internal temperature of 30°–35°C., whereupon agitation was continued for another 3 hours at the same temperature. The reaction mixture was then poured into 800 ml of 5% sodium sulphate solution and the precipitate was filtered off and after drying in vacuo yielded 21.0 g of product in crystal form having a melting point of 71.5°–73.5°C. (yield 90% of theoretical). Recrystallisation from benzine yielded the intermediate 3-(2'-methyl-2'-nitrobutyl)-indole in the form of colourless matted needles, mixed melting point 79.5°–80°C.

Reduction: A mixture of 90.0 g (388 mM) of the nitro intermediate and 9.0 g of palladium catalyst (5% on carbon) and 1000 ml of absolute ethanol was covered with hydrogen at a pressure of 25 atmospheres gauge in the autoclave whereupon it was heated to 70°C. and agitation was continued at this temperature for 7 hours. Filtration, evaporation in vacuo, recrystallisation from xylene and processing of the mother liquor yielded 74.7 g of 3-(2'-amino-2'-methylbutyl)-indole. (Yield: 95% of the theoretical).

Salt formation: The action of ethereal hydrochloric acid on the amine yielded the hydrochloride which, after recrystallisation from acetone/methanol or chloroform/methanol, was obtained in the form of white needles having the melting point of 225.5°–228°C. and which is soluble very satisfactorily in usual alcohols and in water.

Calculated for $C_{13}H_{18}N_2 \cdot HCl$ (238.8) 65.40 C, 8.02 H, 11.73 N, 14.85 Cl.

Found: 65.28 C, 8.14 H, 11.93 N, 14.69 Cl.

Resolution of racemic mixture: Reaction of the amine obtained as the reduction product with ½ equivalent (—)-mandelic acid in ethanol and recrystallisation of the ether-insoluble intermediate from ethanol yielded the mandelic salt of a melting point of 128°–128.5°C. $\alpha_D^{20} = -69.6°$ Calculated for $C_{21}H_{26}N_2O_3$ (354.4) 71.33 C, 7.40 H.

Found: 71.15 C, 7.75 H.

This salt was resolved with ammonia; the base was taken up in ether and precipitated with ethereal hydrochloric acid. Recrystallisation from acetone-methanol yielded the hydrochloride of melting point 225.5° – 226°C, $\alpha_D^{20} = -56°$ (c = 0.97).

Found: 65.35 C, 8.22 H, 11.60 N, 14.82 Cl.

The dextrorotatory hydrochloride was obtained in a similar way.

EXAMPLE 4

Reaction of the nitro-intermediate obtained in accordance with Example 1 or 3, with p-toluenesulphonic acid methyl ester and anhydrous potassium carbonate in boiling xylene followed by recrystallisation from benzine yielded 1-methyl-3-(2'-methyl-2'-nitrobutyl)-indole in the form of colourless needles having a melting point of 75.5°–76°C., in which the strong IR band of the initial material at 3500 cm$^{-1}$ (1-NH) no longer appears.

Calculated for $C_{14}H_{18}N_2O_2$ (246.3) 68.27 C 7.37 H 11.37 N 12.99 O.

Found: 68.14 C 7.31 H 11.43 N 13.14 O.

Reduction in accordance with the process described in Example 1 or 3 yields 1-methyl-3-(2'-methyl-2'-aminobutyl)-indole (melting point uncertain). A salt obtained by reaction of this amine with malic acid melted at 184°–185°C.

Calculated for $C_{14}H_{20}N_2 \cdot \frac{1}{2} C_4H_6O_5$ (175.2) 67.87 C 8.19 H 9.89 N 14.12 O.

Found: 67.72 C 8.32 H 10.01 N 13.96 O.

A possibly isomorphous malic acid salt melted at 215°–220°C (from chloroform-ethanol).

Found: 67.80 C 8.35 H 9.64 N 14.19 O.

EXAMPLE 5

The procedure described in Example 3 applied to 5-fluorogramine and 2-nitrobutane yielded the intermediate product 3-(2'-methyl-2'-nitrobutyl)-5-fluoroindole. Melting point 71°–72°C. (from benzine). Catalytic reduction thereof yielded 3-(2'-methyl-2'-aminobutyl)-5-fluoro-indole; melting point of the hydrochloride salt 248°–250°C. (from isopropanol).

EXAMPLE 6

If the 3-(2'-methyl-2'-nitrobutyl)-5-methoxy-indole obtained as intermediate product in Example 2 is methylated by the procedure described in Example 4 (or by means of sodium hydride and methyl iodide in hexamethyl phosphoric acid triamide), 1-methyl-3-(2'-methyl-2'-nitrobutyl)-5-methoxy-indole is obtained and melts at 95°–96°C. after crystallisation from acetone/water and distillation. Catalytic reduction thereof yields 1-methyl-3-(2'-methyl-2'-aminobutyl)-5-methoxy-indole. Melting point of the benzoic acid salt 179.5°–184°C. (insoluble in ether).

EXAMPLE 7

Reaction of 3-(2'-methyl-2'-nitrobutyl)-indole obtained as intermediate product in Example 1 or 3 with benzyl chloride and sodium hydride in dimethylformamide yields 1-benzyl-3-(2'-methyl-2'-nitrobutyl)-indole having a boiling point of 110°C./0.06 mm Hg. Reduction thereof yields 1-benzyl-3-(2'-methyl-2'-aminobutyl)-indole. The salts formed by reaction of this amine with malic acid having the following melting points M.P. 263.5° –265.5°C. (from ethanol)

Calc. for $C_{20}H_{24}N_2 \cdot C_4H_6O_5$ (426.5): 67.58 C 7.04 H 6.57 N 18.76 O.

Found: 68.06 C 7.30 H 6.47 N 18.17 O.

M.P. 181° – 183°C. (from ethanol/ether)

Calc. for $C_{20}H_{24}N_2 \cdot \frac{1}{2} C_4H_6O_5$ (359.5) 73.50 C 7.57 H 7.79 N 11.13 O.

Found: 73.59 C 7.58 H 7.75 N 11.07 O.

EXAMPLE 8

The 3-(2'-methyl-2'-aminobutyl)-indole obtained as reduction product in accordance with Example 1 or 3 was reacted with phenyl formate to yield 3-(2'-methyl-2'-formylaminobutyl)-indole; melting point 121.5°–124.5°C. (from ether). Reduction thereof with LiAlH$_4$ yielded 3-(2'-methyl-2'-methylaminobutyl)-indole having a melting point of 100°–103°C. (from cyclohexane).

EXAMPLE 9

The reduction product obtained in accordance with Example 1 or 3 was heated to reflux temperature for 1 hour with benzoyl chloride in pyridine, and resulted in 3-(2'-methyl-2'-benzoylaminobutyl)-indole having the melting point 118.5°–119.5°C. (from xylene). Reduction with LiAlH$_4$ yields 3-(2'-methyl-2'-benzylaminobutyl)-indole; melting point of hydrochloride salt 231°–232°C. (from chloroform).

EXAMPLE 10

With the same procedure as in Example 9, using p-chlorobenzoyl chloride instead of benzoyl chloride, 3-(2'-methyl-2'-p-chlorobenzoylaminobutyl)-indole was obtained with a melting point of 158°–160°C. (from benzine). Reduction thereof yielded 3-(2'-methyl-2'-p-chlorobenzylaminobutyl)-indole; melting point of the hydrochloride salt 250°–251°C. (from isopropanol).

EXAMPLE 11

The reduction product obtained in accordance with Example 1 or 3 was heated to reflux temperature with acrylonitrile for 72 hours, 3-(2'-ethyl-2'-β-cyanoethylaminobutyl)-indole forming as product. Melting point of the hydrochloride salt 167°–170°C. (from butanol).

EXAMPLE 12

If the 2-nitrobutane in Example 1 is replaced by the corresponding quantity of 2-nitropentane, using the same procedure as in Example 1, the intermediate product obtained is 3-(2'-methyl-2'-nitropentyl)-indole; melting point 78°–80°C (from petroleum ether). Reduction yielded 3-(2'-methyl-2'-aminopentyl)-indole, which after recrystallisation from petroleum ether yields needle-shaped crystals of a melting point of 73.5° to 74.5°C.

EXAMPLE 13

If the procedure of Example 3 is applied to the corresponding quantity of 3-nitropentane instead of 2-nitrobutane, 3-(2'-ethyl-2'-nitrobutyl)-indole is initially obtained with a melting point of 92°–94°C. (from benzine). Reduction yields 3-(2'-ethyl-2'-aminobutyl)-indole with a melting point of 130.5°–131.5°C. (from CCl$_4$).

EXAMPLE 14

If the corresponding quantity of 4-nitroheptane is used instead of 2-nitrobutane with the procedure according to Example 3, 3-(2'-propyl-2'-nitropentyl)-indole is initially obtained; melting point 87°–89°C. (from benzine). Reduction thereof yields 3-(2'-propyl-2'-aminopentyl)-indole; melting point of the hydrochloride salt 215°–217°C. (from acetone).

We claim:

1. A method of inhibiting or reducing appetite in a mammal or a human comprising administering to said mammal or human in need of such treatment an effective amount of a compound selected from the class consisting of 3-(2'-amino-2'-methylbutyl)-indole and its pharmaceutically acceptable nontoxic acid addition salts.

* * * * *